(12) United States Patent
Rill et al.

(10) Patent No.: US 10,653,557 B2
(45) Date of Patent: May 19, 2020

(54) OPHTHALMOLOGICAL LASER THERAPY DEVICE FOR PRODUCING CORNEAL ACCESS INCISIONS

(71) Applicant: Carl Zeiss Meditec AG, Jena (DE)

(72) Inventors: Michael Stefan Rill, Jena (DE); Delbert Peter Andrews, Oberkochen (DE); Tobias Damm, München (DE); Rupert Menapace, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 144 days.

(21) Appl. No.: 15/553,163

(22) PCT Filed: Feb. 23, 2016

(86) PCT No.: PCT/EP2016/053707
§ 371 (c)(1),
(2) Date: Aug. 23, 2017

(87) PCT Pub. No.: WO2016/135111
PCT Pub. Date: Sep. 1, 2016

(65) Prior Publication Data
US 2018/0110654 A1    Apr. 26, 2018

(30) Foreign Application Priority Data

Feb. 27, 2015 (DE) .................. 10 2015 002 729

(51) Int. Cl.
*A61F 9/008*    (2006.01)
(52) U.S. Cl.
CPC ...... *A61F 9/00825* (2013.01); *A61F 9/00838* (2013.01); *A61F 9/00834* (2013.01);
(Continued)
(58) Field of Classification Search
CPC .............. A61F 9/00825; A61F 9/00838; A61F 9/00834
See application file for complete search history.

(56) References Cited

U.S. PATENT DOCUMENTS 7,493,153 B2 * 2/2009 Ahmed ................ G02B 27/017
345/7
2002/0173779 A1 * 11/2002 Donitzky ................ A61F 9/008
606/5
(Continued)

FOREIGN PATENT DOCUMENTS

DE    10 2005 014 760 A1    10/2006
DE    10 2013 004 688 A1    9/2014
(Continued)

OTHER PUBLICATIONS

English translation of PCT International Preliminary Report on Patentability and Written Opinion for International Application No. PCT/EP2015/053707, dated Sep. 8, 2017, 9 pages.
(Continued)

*Primary Examiner* — Christopher A Flory
(74) *Attorney, Agent, or Firm* — Patterson Thuente Pedersen, P.A.

(57) ABSTRACT

An ophthalmological laser therapy device having a pulsed laser, a positioning system and a control system that produce incisions in a tissue of an eye, in particular for producing corneal access incisions and a corresponding method. The invention produces corneal access incisions having increased leak tightness under external influences. Compressive strength, and complex incision geometries can be realized. An ophthalmological laser therapy device has a control system which is programmed to vary the operating parameters of the laser system and/or of the positioning system on the basis of a local position of the focal volume of a laser beam in the corneal tissue such that the access incision in the corneal tissue is varied and/or interrupted in the width of the access incision. The invention further includes a corresponding computer program product and a
(Continued)

method for performing a corneal access incision in a corneal tissue of an eye.

9 Claims, 7 Drawing Sheets

(52) U.S. Cl.
CPC .............. *A61F 2009/0087* (2013.01); *A61F 2009/00872* (2013.01); *A61F 2009/00887* (2013.01); *A61F 2009/00891* (2013.01); *A61F 2009/00897* (2013.01)

(56) References Cited

U.S. PATENT DOCUMENTS

| | | | | |
|---|---|---|---|---|
| 2003/0169603 A1* | 9/2003 | Luloh | A61B 90/36 | 362/574 |
| 2004/0102729 A1* | 5/2004 | Haffner | A61F 9/00781 | 604/8 |
| 2004/0254454 A1* | 12/2004 | Kockro | A61B 90/36 | 600/424 |
| 2005/0015005 A1* | 1/2005 | Kockro | A61B 90/36 | 600/427 |
| 2005/0203367 A1* | 9/2005 | Ahmed | G02B 27/017 | 600/407 |
| 2006/0100612 A1* | 5/2006 | van der Heyd | A61F 2/142 | 606/4 |
| 2007/0236514 A1* | 10/2007 | Agusanto | A61B 1/00193 | 345/646 |
| 2007/0238981 A1* | 10/2007 | Zhu | A61B 90/36 | 600/424 |
| 2008/0058777 A1* | 3/2008 | Kurtz | A61F 9/008 | 606/4 |
| 2008/0065052 A1* | 3/2008 | Bischoff | A61F 9/00827 | 606/4 |
| 2008/0275433 A1* | 11/2008 | Russmann | A61F 9/008 | 606/5 |
| 2008/0297535 A1* | 12/2008 | Reinig | G02B 27/2235 | 345/633 |
| 2009/0182312 A1* | 7/2009 | Gertner | A61F 9/008 | 606/4 |
| 2010/0208202 A1* | 8/2010 | Itoh | A61B 3/12 | 351/206 |
| 2010/0228119 A1* | 9/2010 | Brennan | A61B 5/0066 | 600/424 |
| 2010/0228249 A1* | 9/2010 | Mohr | A61B 34/37 | 606/41 |
| 2010/0324542 A1* | 12/2010 | Kurtz | A61F 9/008 | 606/6 |
| 2010/0331831 A1* | 12/2010 | Bischoff | A61F 9/008 | 606/5 |
| 2011/0106102 A1* | 5/2011 | Balicki | A61B 3/1005 | 606/130 |
| 2011/0118609 A1* | 5/2011 | Goldshleger | A61F 9/00834 | 600/476 |
| 2011/0137299 A1* | 6/2011 | Donitzky | A61F 9/008 | 606/4 |
| 2011/0184394 A1* | 7/2011 | Donitzky | A61F 9/008 | 606/5 |
| 2011/0251601 A1* | 10/2011 | Bissmann | A61F 9/00831 | 606/5 |
| 2011/0282331 A1* | 11/2011 | Brennan | A61B 3/102 | 606/4 |
| 2012/0071891 A1* | 3/2012 | Itkowitz | B25J 13/084 | 606/130 |
| 2012/0083775 A1* | 4/2012 | Donitzky | A61F 9/00804 | 606/5 |
| 2012/0184846 A1* | 7/2012 | Izatt | G02B 21/0012 | 600/425 |
| 2012/0226150 A1* | 9/2012 | Balicki | A61B 5/0066 | 600/424 |
| 2012/0281236 A1* | 11/2012 | Kang | G01B 9/02044 | 356/479 |
| 2012/0310224 A1* | 12/2012 | Miyagi | A61F 9/00827 | 606/5 |
| 2013/0038836 A1* | 2/2013 | Smith | A61B 3/0008 | 351/211 |
| 2013/0072916 A1* | 3/2013 | Bischoff | A61F 9/008 | 606/5 |
| 2013/0119029 A1* | 5/2013 | Bischoff | A61F 9/00827 | 219/121.83 |
| 2013/0217967 A1* | 8/2013 | Mohr | A61B 34/37 | 600/109 |
| 2013/0245375 A1* | 9/2013 | DiMaio | A61B 34/10 | 600/111 |
| 2013/0265542 A1* | 10/2013 | Frey | A61F 9/008 | 351/206 |
| 2013/0281817 A1* | 10/2013 | Schaller | A61B 3/1005 | 600/398 |
| 2013/0281992 A1* | 10/2013 | Seiler | A61F 9/00827 | 606/5 |
| 2014/0005484 A1* | 1/2014 | Charles | A61B 17/02 | 600/201 |
| 2014/0094968 A1* | 4/2014 | Taylor | B25J 13/006 | 700/257 |
| 2014/0114297 A1* | 4/2014 | Woodley | A61F 9/008 | 606/6 |
| 2014/0160264 A1* | 6/2014 | Taylor | G02B 21/008 | 348/79 |
| 2014/0221822 A1* | 8/2014 | Ehlers | A61B 5/061 | 600/424 |
| 2014/0257258 A1* | 9/2014 | Kurtz | A61F 9/008 | 606/4 |
| 2014/0307078 A1* | 10/2014 | Charles | A61B 3/102 | 348/78 |
| 2014/0316389 A1* | 10/2014 | Schuele | A61F 9/00804 | 606/5 |
| 2015/0025510 A1* | 1/2015 | Vogler | A61F 9/00825 | 606/4 |
| 2015/0209527 A1* | 7/2015 | Kang | A61M 5/46 | 604/506 |
| 2015/0272782 A1* | 10/2015 | Schuele | A61F 9/00754 | 606/5 |
| 2015/0297403 A1* | 10/2015 | Kurtz | A61F 2/142 | 606/5 |
| 2015/0297404 A1* | 10/2015 | Kang | A61F 9/00736 | 606/166 |
| 2015/0305941 A1* | 10/2015 | Donitzky | A61F 9/00825 | 606/4 |
| 2015/0342460 A1* | 12/2015 | Izatt | G02B 21/0012 | 600/411 |
| 2015/0342695 A1* | 12/2015 | He | G01L 5/166 | 606/130 |
| 2015/0342698 A1* | 12/2015 | Eslami | A61F 9/00727 | 606/130 |
| 2015/0374548 A1* | 12/2015 | Wottke | A61F 9/00827 | 606/5 |
| 2016/0030240 A1* | 2/2016 | Gonenc | G01L 5/226 | 604/95.01 |
| 2016/0074220 A1* | 3/2016 | Ianchulev | A61B 18/082 | 606/107 |
| 2016/0074225 A1* | 3/2016 | Spooner | A61F 9/00827 | 606/5 |
| 2016/0174834 A1* | 6/2016 | Eslami | A61B 3/102 | 351/206 |
| 2016/0250068 A1* | 9/2016 | Dewey | A61F 9/009 | 606/4 |
| 2016/0262605 A1* | 9/2016 | Taylor | A61B 3/13 | |
| 2016/0324593 A1* | 11/2016 | El-Haddad | G06T 7/73 | |

(56) References Cited

U.S. PATENT DOCUMENTS

2017/0087022 A1* 3/2017 Kurtz .................. A61F 9/008
2018/0071144 A1* 3/2018 Naranjo-Tackman .....................
                                                        A61F 9/00829
2018/0104104 A1* 4/2018 Gray ................ A61F 9/00827

FOREIGN PATENT DOCUMENTS

WO    WO 2004/017878 A1    3/2004
WO    WO 2008/030699 A2    3/2008

OTHER PUBLICATIONS

PCT International Search Report and Written Opinion for International Application No. PCT/EP2015/053707, dated May 18, 2016, 15 pages.
English translation of PCT International Search Report for International Application No. PCT/EP2015/053707, dated May 18, 2016, 3 pages.
DE Search Report for DE 10 2015 002 729.8, dated Sep. 11, 2015, 18 pages.
David W. Langerman, "Architectural design of a self-sealing corneal tunnel, single hinge incision" (J Cataract Refract Surg 20, 1994), pp. 84-88.

* cited by examiner

State of the Art

Fig. 2a  Fig. 2b

State of the Art

Fig. 7

OPHTHALMOLOGICAL LASER THERAPY DEVICE FOR PRODUCING CORNEAL ACCESS INCISIONS

RELATED APPLICATIONS

This application is a National Phase entry of PCT Application No. PCT/EP2016/053707 filed Feb. 23, 2016 which application claims the benefit of priority to German Application No. 10 2015 002 729.8, filed Feb. 27, 2015, the entire disclosures of which are incorporated herein by reference.

FIELD OF THE INVENTION

The present invention relates to an ophthalmological laser therapy device, composed of a laser system for generating a pulsed laser beam, a positioning system for spatial displacement of a focal volume of the laser beam, and a control system for controlling the working parameters of the positioning system and/or the laser system, with which the tissues of an eye can be worked on, such that incisions can be generated in the eye tissues. In particular, corneal access incisions can be produced with this ophthalmological laser therapy device.

The invention further relates to a computer program product and a method for executing a corneal access incision in corneal tissue of an eye.

BACKGROUND

It has become the standard practice in eye surgery to use laser systems to assist in the individual steps of a surgical process. The interaction of the laser with the eye tissue, by which the tissue can be separated, replaces the formerly normal incisions with a scalpel. The laser systems are thus a component of ophthalmological therapy systems.

Femtosecond (fs) laser systems are frequently used for making incisions in eye tissue. In particular, such femtosecond laser systems are also used to make incisions in lens tissue afflicted with cataracts. For a portion of the laser cataract surgery, the surgeon requires direct access to the lens of the patient via the cornea, i.e. through the corneal tissue. This access can likewise be obtained using a laser beam. Such access incisions in the eye operations. On one hand, they must be small, such that the risk of infection is reduced. On the other hand, the access incision should be placed such that the aqueous humor cannot drain out. In particular, drainage must be prevented even under the influence of direct external mechanical effects. An important thing here is the fact that following such an incision, only the thin corneal epithelium heals. In the first days and weeks following the operation, the thick corneal stroma tissue is only "glued" together by adhesion forces. The stroma tissue is the middle corneal layer, and forms ca. 90% of the overall cornea thickness. For this reason, the wound may open due to external effects, e.g. pressure applied to the eyeball.

Figure 1A:
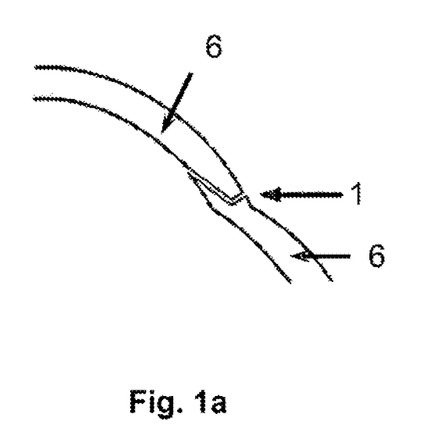
FIG. 1a depicts a corneal access incision according to the prior art.
Figure 1B:
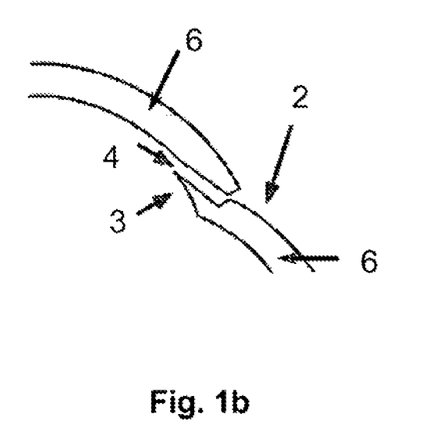
FIG. 1b depicts its behavior when subjected to small external pressures, as described above.

Complex, discontinuous corneal access incisions are difficult or impossible to execute with a scalpel. For this reason, it is standard practice to execute these incisions with a laser. However, known solutions can only obtain relatively simple incision geometries. FIG. 1a shows a currently typical bi-planar corneal access incision 1, i.e. an access incision 1 along two planes. Such corneal access incisions 1 as those shown in FIG. 1a have the disadvantage, however, that they lose their sealing properties when the eye is subjected to external mechanical effects, such that aqueous humor can drain out of the eye, or germs can penetrate, as is depicted in FIG. 1b, showing the effects of an external pressure 2 on the eyeball: An external pressure 2 results in an increase in the internal pressure in the eye (intra-ocular pressure IOP) 3. With an access incision 1 according to FIG. 1a, this results in turn in a leak 4, through which the aqueous humor can then escape. This problem persists long after the operation.

Figure 2A:
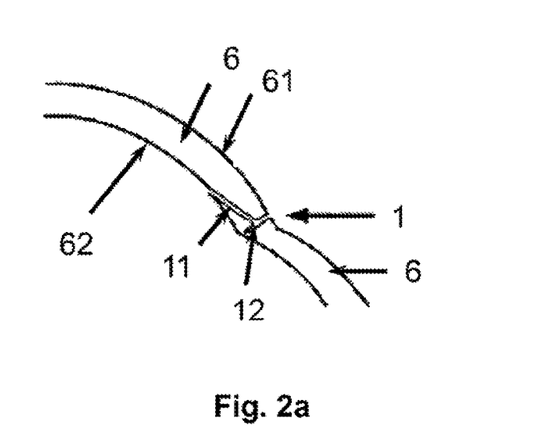
FIG. 2a depicts another corneal access incision according to the prior art.

In the publication by David W. Langerman, "Architectural design of a self-sealing corneal tunnel, single hinge incision" (J Cataract Refract Surg 20, 1994), a special incision geometry for a corneal access incision 1 is presented. It differs from the incision geometry of the conventional corneal access incisions: The corneal access incision 1 of Langerman comprises, in addition to a bi-planar incision 11 in the corneal tissue 6 of the eye, first starting from an outer boundary surface 61 at approximately a right angle, then running in a suitable plane to an inner boundary surface 62, consequently forming a "tunnel," an additional deep vertical partial incision 12, which, starting from the bi-planar incision 11, extends toward the inner boundary surface 62, without reaching it, however, see FIG. 2a. This additional vertical partial incision 12 results in the formation of a wedge-shaped valve flap with a hinge 5, close to the inner surface of the cornea. This incision is made manually, according to Langerman.

Figure 2B:
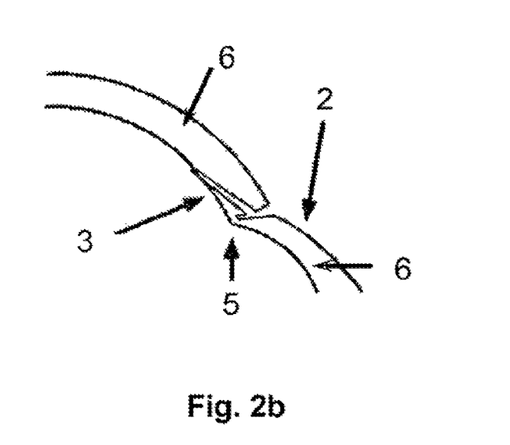
FIG. 2b depicts its behavior when subjected to small external pressures, as described above.

With a punctiform pressure 2 in the region of the outer "tunnel entrance" of the access incision 1 formed as a tunnel, composed of the bi-planar incision 11 and the deep vertical partial incision 12, the deformation and thus the opening of the tunnel can no longer continue along the floor of the tunnel to the inner "tunnel exit" and thus open the "corneal valve," allowing aqueous humor to drain out of the eye. Instead, the wedge-shaped valve flap then swings upward on the hinge 5, and is pressed against the roof of the tunnel by the intra-ocular pressure 3. The result is an improvement in the "deformation stability" of the incision. FIG. 2b shows how such an access incision behaves when subjected to moderate external forces. The hinge 5 increases the tissue flexibility, such that the bonded corneal tissue 6 does not separate, and the access wound thus remains closed. This incision geometry thus offers a decisive medical advantage.

With higher pressure, however, this corneal access incision does not remain sealed. The "raising" of the wedge-shaped valve flap on the hinge, and thus the closing of the tunnel, is strongly limited by the space along the vertical partial incision and by the elasticity of the corneal tissue.

Furthermore, such an incision geometry did not become established in the past because it was very difficult to implement with a scalpel due to the limited thickness of the cornea.

SUMMARY

Embodiments of the present invention include an ophthalmological laser therapy device and a method for executing a corneal access incision in corneal tissue of an eye, with which corneal access incisions can be produced such that their sealing, in particular their compressive strength, is increased when subjected to external effects, and complex incision geometries can be implemented, and to illustrate corresponding incision geometries.

An ophthalmological laser therapy device comprises a laser system, which is configured to generate a pulsed laser beam. Such a pulsed laser enables high light intensities to be generated, i.e. a very fast release of the stored energy. Pulsed lasers are used in material processing, among other things. One of the fields of application is ophthalmology. In ophthalmology, incisions in an eye tissue, e.g. the cornea or lens of the eye, can be made through photodisruption. The photodisruption takes place only in the focal volume due to the multi-photon absorption of the laser beam. Due to a strong non-linear increase in the absorption of the laser light, an optical penetration takes place, in which a plasma is formed, resulting in separation of the material.

Moreover, the ophthalmological laser therapy device comprises a positioning system, which is configured for spatial displacement of a focal volume of the laser beam into a target region. Such a target region can be the corneal tissue of the eye, as well as another tissue of the eye. The lens as well can theoretically be worked on with such a laser therapy device. Thus, the pulsed laser beam is deflected accordingly by the positioning system. As a result of the possibility of deflection, or displacement, of the laser beam, "incisions" can be made in the target region along defined structures or patterns.

In order to control the positioning system and/or the laser system, thus to have an effect on the working parameters of the positioning system and/or the laser system, the ophthalmological laser therapy system includes a control system. The control system can comprise a single unit thereby. Alternatively, the control system may also include numerous components, distributed over the ophthalmological therapy device, which may be interconnected to one another, if applicable.

The control system is then programmed, according to the invention, to modify the working parameters of the laser system and/or the positioning system as a function of a spatial position of the focal volume of the laser beam in the corneal tissue, in order to generate a corneal access incision in corneal tissue of an eye through photodisruption, such that the access incision in the corneal tissue is varied in terms of its width and/or the access incision is interrupted. This can also mean that only portions of the access incision are varied in terms of their width, or interrupted.

A corneal access incision is defined thereby, in that it opens a passage, or "tunnel" through the cornea, from an outer boundary surface of the cornea to an inner boundary surface of the cornea, through which an instrument having a small diameter, e.g. a suction tube or an applicator containing an artificial lens in a folded state can be inserted into the ocular chamber. Its incision geometry can be of a very complex nature. It can include, in addition to the "tunnel," normally formed by a bi-planar incision, further secondary incisions, which improve the function of the access incision of forming an opening for inserting instruments, but simultaneously ensure a reliable sealing of the access incision after the operation. Whether or not a secondary incision belongs to a corneal access incision is defined thereby through the intended effect of this secondary incision on the functioning of the corneal access incision. A secondary incision also belongs to a corneal access incision when there is an interruption of the access incision between the bi-planar incision passing through the corneal tissue and the corresponding secondary incision, as long as it contributes to the functioning of the corneal access incision.

In order to then be able to vary the complex access incision in terms of its incision width, or to potentially also generate secondary incisions, not connected to the "tunnel," but still belonging to the corneal access incision, the control system is programmed to constantly adjust working parameters for the positioning system and/or the laser system during the step in which the corneal access incision is generated as a function of the respective position of the focus, or focal volume of the laser beam in the corneal tissue, thus the volume in which a separation of corneal tissue can take place by application of photodisruption, in order to generate a corresponding incision pattern for a corneal access incision, which is intermittently interrupted and/or in which the incision width is varied at least in sub-regions.

For the laser system, this concerns working parameters like the power of each laser pulse, the pulse duration, the peak intensity, and the repetition rate of the laser, for example.

The incision width, on the other hand, can be influenced via the positioning system, e.g. through a change in the speed of the deflection or displacement of the laser beam, and thus the speed of the movement of the focal volume of the laser beam through the corneal tissue, or through numerous changes in direction of the movement of the focal volume of the laser beam through the corneal tissue, by application of which a sub-section of the corneal access incision is "retraced" repeatedly.

The programming of the control system, i.e. its encoding for the step in which the corneal access incision is generated, can access standard templates of an eye in a simple example embodiment, which are selected from examination data of the eye that is to be operated on, which have been compiled in advance with an examination system, e.g. an OCT (optical coherence tomography) system or a mapping system according to the Scheimpflug principle, or a light-section method.

In an example design, the control system takes examination data into account directly, such as the position of the eye structures, the diameter of the eye body, and the corneal thickness, for example, in that the modifications of the working parameters of laser systems and/or positioning systems are encoded as a function of specific examination data, which must be provided to the control system of the ophthalmological laser therapy device in each operation for the step in which the corneal access incision is generated.

In an advantageous example embodiment, the control system of the ophthalmological laser therapy device is programmed to modify the working parameters of the laser system and/or positioning system such that a bi-planar incision is generated in the corneal tissue, which thus passes through the corneal tissue from an outer boundary surface to an inner boundary surface, and a vertical, wedge-shaped partial incision is generated that tapers toward the end, starting from this bi-planar incision.

The sequence in which the two incisions are generated, thus the bi-planar incision and the vertical partial incision, as components of a complex corneal access incision, is not important. The vertical partial incision can even be generated during the generation of the bi-planar incision. The vertical partial incision starts for example close to the position in the bi-planar incision where the bi-planar incision changes directions, thus close to the transition of the perpendicular incision into an incision running diagonally through the corneal tissue. In such a configuration, the effect of the hinge and the wedge-shaped valve flap is particularly great, because with mechanical effects such as an external pressure, the valve flap can close over the entire area of the bi-planar incision.

The vertical partial incision can vary in terms of its length or depth, as well as in terms of the extent of the tapering, but it must not penetrate the inner boundary surface of the corneal tissue. The angle of the second part of the bi-planar incision can also vary. This part of the bi-planar incision is for example curved slightly, such that the valve flap resulting thereby is slightly convex.

In an alternative second example embodiment, the control system of the ophthalmological laser therapy device is programmed to modify the working parameters of the laser system and/or positioning system, such that a bi-planar incision and an inner vertical partial incision, not directly connected therewith, is generated in the region of the bi-planar incision in the corneal tissue.

Here as well, the sequence in which the two incision are generated, i.e. the bi-planar incision and the inner vertical partial incision, as components of a complex corneal access incision, is unimportant. The inner vertical partial incision should for example start from an inner boundary surface of the corneal tissue close to the position in the bi-planar incision where the bi-planar incision changes directions. Here as well, the effect of the hinge and the wedge-shaped valve flap is particularly strong, because with mechanical effects, such as an external pressure, the valve flap can close over the entire diagonal area of the bi-planar incision.

The length or the depth of the inner vertical partial incision, starting from the inner boundary surface of the corneal tissue, as well as the incision width, can vary. It cannot, however, intersect with the bi-planar incision, or extend to the outer boundary surface of the corneal tissue. The angle of the second part of the bi-planar incision can likewise vary. This part of the bi-planar incision, in turn, is for example slightly curved, such that the resulting valve flap is slightly convex.

In a third alternative example embodiment, the control system of the ophthalmological laser therapy device is programmed to modify the working parameters of the laser system and/or positioning system, such that a bi-planar incision and an outer vertical partial incision in the region of the bi-planar incision, not directly connected thereto, are generated in the corneal tissue.

This embodiment can also be regarded as a supplementary embodiment, in which, in addition to the bi-planar incision and an inner vertical partial incision, at least one supplementary outer vertical partial incision is programmed in the control system of the ophthalmological laser therapy device.

The sequence in which the incisions are generated, thus the bi-planar incision, the inner vertical partial incision and the outer vertical partial incision, as components of a complex corneal access incision, is not important. The outer vertical partial incision for example starts on an outer boundary surface of the corneal tissue close to the region of the bi-planar incision.

As with the other embodiments, the third example embodiment in particular is not limited thereby to the generation of a single outer vertical partial incision: It is also possible to program the control system to generate numerous outer vertical partial incisions in the corneal tissue, either on both sides of the bi-planar incision or on just one side of the bi-planar incision.

The outer vertical partial incision can be straight incision. The outer vertical partial incision is for example programmed, however, such that it is wedge-shaped, i.e. tapering from the outer boundary surface of the corneal tissue inward. The length or depth of the outer vertical partial incision starting from the outer boundary surface of the corneal tissue, can vary, but it cannot intersect with the bi-planar incision or reach the inner boundary surface of the corneal tissue. The angle of the first part of the bi-planar incision can also vary. This part of the bi-planar incision is for example slightly curved, such that the resulting valve flap is slightly convex.

The ophthalmological laser therapy device for example includes a femtosecond (fs) laser system, thus an ultra-short pulse laser system.

The ophthalmological laser therapy device for example includes a control system, comprising an interface for receiving and transmitting examination data of an eye from an examination system. Such an examination system can be an OCT system, an ultrasound system, a Scheimpflug camera, or a microscope, for example, which generates the examination data in a first variation outside an ophthalmological laser therapy device in an examination taking place shortly before the therapy, such that these data can be made available to the ophthalmological therapy device via the control system interface. This can take place through manually entering the data, or through an automatic data transfer.

In an alternative variation, the ophthalmological laser therapy device includes an examination system for generating examination data of the eye. Examples of such an examination system are an OCT system, an ultrasound system, a Scheimpflug camera, or a surgical microscope. The ophthalmological therapy device can also include numerous examination systems, which supply examination data simultaneously or successively. The examination data generated by such an examination system can be supplied in turn to the ophthalmological laser therapy device via a control system interface. Such an interface can function substantially more automatically compared to when external examination data are used. The control system can consequently also be configured such that it can access the examination system directly.

It is for example possible to nevertheless take examination data from an external examination system into account, even when the ophthalmological laser therapy device includes one or more internal examination systems.

If an ophthalmological laser therapy device includes an examination system for generating examination data of an eye, then it can furthermore be configured to control the generation of a corneal access incision by use of examination data from the examination system. For this, it is possible to use a closed loop control for generating the corneal access incision, i.e. the examination data are further enhanced during the generation of the corneal access incision, and used, if applicable, for making corrections to the generation of the corneal access incision.

The positioning system of an ophthalmological laser therapy device, which is responsible for deflecting and/or displacing the laser beam, and thus the focus, toward a desired location in an eye, for example includes for this at least one of the following components: a stationary or rotatable mirror, lens, or directional module.

In a method for executing a corneal access incision in corneal tissue of an eye, a bi-planar incision and a vertical partial incision are generated. The bi-planar incision is generated such that it opens up a "tunnel" through the cornea from an outer boundary surface of the cornea to an inner boundary surface of the cornea, through which instruments having a small diameter can be inserted into the ocular chambers. It for example comprises a first steep part and a second, strongly angled part. The angles of the bi-planar incision can vary. The second angled part of the bi-planar incision may be slightly curved.

The sequence in which the two incision are generated, i.e. the bi-planar incision and the vertical partial incision, as components of a complex corneal access incision, is unimportant. The vertical partial incision can even be generated during the generation of the bi-planar incision.

The vertical partial incision is a secondary incision, which improves the functioning of the access incision regarding the formation of an opening for inserting instruments, as well as simultaneously ensuring a reliable closure of the access point following the operation.

According to the invention, in a first alternative of the method, the vertical partial incision is generated such that it is connected directly to the bi-planar incision, and has a wedge-shaped profile, tapering toward the end facing away from the bi-planar incision.

The vertical partial incision for example starts close to the point in the bi-planar incision where the bi-planar incision changes directions, thus the transition from the perpendicular incision to an incision running diagonally through the corneal tissue.

The vertical partial incision can vary in terms of its length or depth, as well as the angle of the wedge, but it cannot extend to the inner boundary surface of the corneal tissue, in order to ensure the necessary stability of the cornea.

In a second alternative of the method according to the invention, the vertical partial incision is disposed in a region of the bi-planar incision such that the vertical partial incision is not, however, connected directly to the bi-planar incision.

In a first variation of the second alternative, the vertical partial incision is generated such that it starts from the inner boundary surface of the corneal tissue, for example close to the point in the bi-planar incision where the bi-planer incision changes directions.

The inner vertical partial incision can vary in terms of its length or depth, starting from the inner boundary surface of the corneal tissue, as well as in terms of the width of the incision, but it cannot intersect with the bi-planar incision or reach the outer boundary surface of the corneal tissue.

In a second variation of the second alternative of the method according to the invention, the vertical partial incision is generated such that it starts on the outer boundary surface of the corneal tissue. It can vary in terms of its length, depth and incision width, but it cannot intersect with the bi-planar incision or reach the inner boundary surface of the corneal tissue. The outer vertical partial incision is for example wedge-shaped.

In theory, numerous outer vertical partial incisions, or a combination of outer and inner vertical incisions can also be generated, in order to contribute to an optimal functioning of the corneal access incision, as described above.

This method is for example executed with an ophthalmological laser therapy device set to generate a pulsed laser beam.

This method is for example executed with an ophthalmological laser therapy device described above.

In contrast to corneal access incisions manually carried out with a scalpel, it is possible with pulsed lasers, in particular femtosecond lasers, to execute complex, unconnected incisions, because the laser/tissue interaction only takes place in the focal point of the laser beam.

The use of such ophthalmological laser therapy systems and the corneal access incisions described above does not extend thereby to cataract surgery. They can be used in general in ophthalmology, e.g. in trauma surgery and for glaucoma interventions.

The proposed incision geometries offer the advantage, in comparison with conventional bi-planar access incisions, that corneal wounds do no reopen even when subjected to stronger external forces. Although it is difficult to make the incisions with a scalpel, they can be readily produced using a pulsed laser, e.g. a femtosecond laser.

A computer program product according to the invention is configured to execute the method described herein for executing a corneal access incision in corneal tissue of an eye on an ophthalmological laser therapy device. In order to generate such a corneal access incision, the computer program product is installed on an ophthalmological laser therapy device, in particular on an ophthalmological laser therapy device that includes a laser system for generating a pulsed laser beam, a positioning system for spatial displacement of a focal volume of the laser beam into a target region, and a control system for controlling the working parameters of the positioning system and/or the working parameters of the laser system. This is for example a laser therapy device according to the invention.

The computer program product is for example configured to modify working parameters of a positioning system and/or a laser system of the ophthalmological laser therapy device by application of a control system of the ophthalmological laser therapy device as a function of a spatial position of the focal volume in the corneal tissue of the eye such that an incision width of the corneal access incision generated by photodisruption is varied as a function of the spatial position in the corneal tissue, and/or the incision is interrupted in places.

BRIEF DESCRIPTION OF THE DRAWINGS

The present invention shall now be explained on the basis of example embodiments. Therein.

DETAILED DESCRIPTION

Figure 3A:
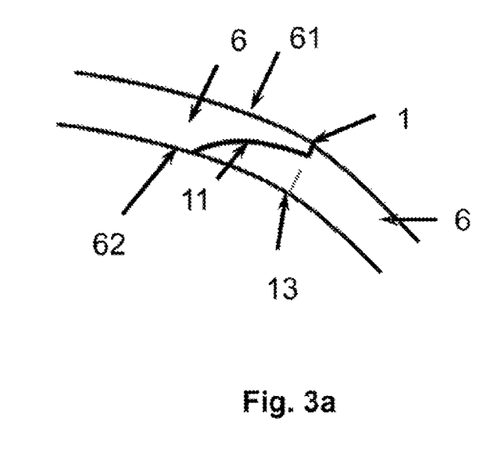
FIG. 3a depicts a first example embodiment of a corneal access incision according to the invention, generated with a first example embodiment of an ophthalmological therapy device according to the invention.

FIG. 3a depicts a first embodiment of a corneal access incision 1 according to an example embodiment of the invention, in corneal tissue 6 of an eye 600. It is the result of a method according to the invention, or a use of the computer program product according to the invention, and in particular, is a use of an ophthalmological laser therapy device 100 according to the invention in a first concrete embodiment, in which the control system 400 is programmed, on one hand, to control the spatial course shown here, of the corneal access incision 1 as a function of the size of the eyeball and the thickness of the cornea, and on the other hand, it is ensured through an accordingly programmed temporary interruption of the laser beam generation during the step for generating the corneal access incision 1, that there is an interruption in the incision between a bi-planar incision 11 and an inner vertical partial incision 13, which collectively form the corneal access incision 1.

The bi-planar incision 11 runs thereby as a "tunnel" through the corneal tissue 6 from an outer boundary surface 61 of the corneal tissue 6 to an inner boundary surface 62 of the corneal tissue 6. Thin instruments can be inserted through it into the ocular chambers. The inner vertical partial incision 13, that runs, starting from an inner boundary surface 62, toward the outer boundary surface 61, but does not reach this surface, and is not connected directly to the bi-planar incision 11, improves the functioning of the access incision.

Figure 3B:
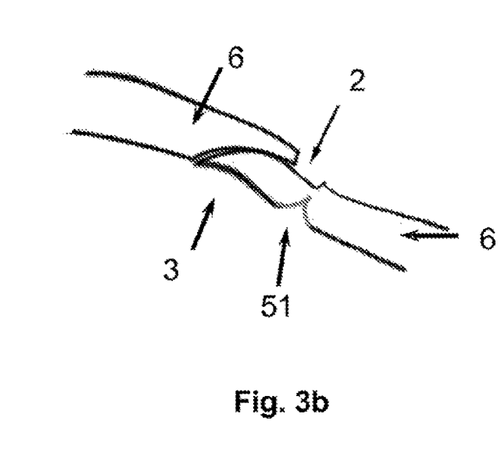
FIG. 3b depicts the behavior of the access incision when subjected to external pressure.

FIG. 3b shows the behavior of the corneal access incision 1 illustrated in FIG. 3a when subjected to external pressure: When an external pressure 2 is exerted on the eyeball, the hinge 51, also referred to as a "posterior hinge," which acts more or less as an expansion point, offers substantially more flexibility than the Langerman incision geometry illustrated in FIGS. 2a and 2b, in terms of keeping the wound closed, despite the increase in the inner pressure 3 in the eye resulting from the external pressure 2.

Figure 4:
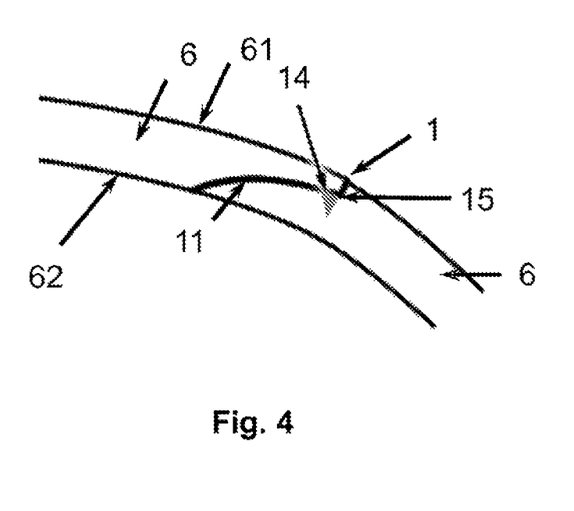
FIG. 4 depicts a second example embodiment of a corneal access incision according to the invention, generated with a second example embodiment of an ophthalmological therapy device according to the invention.

FIG. 4 shows a second example embodiment of a corneal access incision 1 according to the invention, in corneal tissue 6 of an eye 600. It is the result of a method according to the invention, or a use of the computer program product according to the invention, and in particular, is a use of an ophthalmological laser therapy device 100 according to the invention in a second concrete embodiment. On one hand, the spatial course of the corneal access incision 1 shown here is programmed in a control system 400, as a function of the size of the eyeball, and the thickness of the cornea. On the other hand, the width of the incision is varied as a function of the spatial course through a modification of the laser beam intensity programmed accordingly, and thus also generates, in addition to a bi-planar incision 11, a wedge-shaped vertical partial incision 14: Starting from the outer boundary surface 61 of corneal tissue 6 of an eye 600, the focal point of a femtosecond laser is moved with a uniform laser beam intensity perpendicularly into the corneal tissue 6, which generates an incision having a uniform incision width, as the first part of the bi-planar incision 11. At the point 15 where the bi-planar incision 11 changes directions, an abruptly increased laser beam intensity is first steered further in the perpendicular direction, but with a continuous reduction in the laser beam intensity, starting at this maximum value. The focal point of the femtosecond laser is subsequently returned to the point 15 where it changes directions by the positioning system, and executes from there the second part of the bi-planar incision 11, diagonally into the corneal tissue 6, with a slightly curved shape, until reaching the inner boundary surface 61 while using the same, uniform laser beam intensity that was used for the first part of the bi-planar incision 11.

The corneal access incision 1 thus comprises a bi-planar incision 11 formed as a "tunnel" through the corneal tissue 6 from an outer boundary surface 61 of the corneal tissue 6 to an inner boundary surface 62 of the corneal tissue, and a wedge-shaped vertical partial incision 14 tapering toward the end, which is connected directly to the bi-planar incision 11. As a result of this wedge-shaped vertical partial incision 14, the functioning of the access incision 1 is improved insofar as that when it is subjected to external mechanical effects, e.g. an external pressure, the hinge formed at the location of the vertical partial incision 14 is substantially more flexible, and the resulting wedge, i.e. the "valve flap" is pressed upward against the "tunnel ceiling" of the bi-planar incision 11, or can be bent, securely closing the wound, even when subjected to high pressure, and prevents drainage of the aqueous humor.

Figure 5:
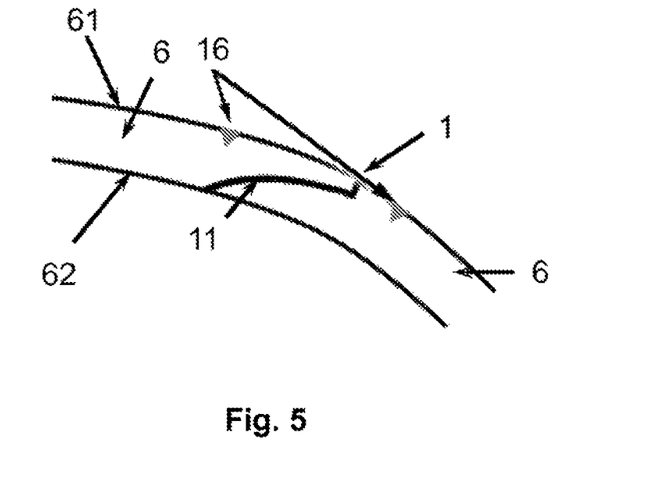
FIG. 5 depicts a third example embodiment of a corneal access incision according to the invention, generated with a third example embodiment of an ophthalmological therapy device according to the invention.

FIG. 5 shows a third example embodiment of a corneal access incision 1 according to the invention, in corneal tissue 6 of an eye 600, which in turn is the result of a method according to the invention, or a use of the computer program product according to the invention, and in particular, is a use of an ophthalmological laser therapy device 100 according to the invention in a third concrete embodiment, in which, on one hand, the spatial course shown here of the corneal access incision 1 is programmed in the control system 400 as a function of the size of the eyeball and the thickness of the cornea, and on the other hand, it is ensured through an accordingly programmed temporary interruption of the laser beam generation during the step for generating the corneal access incision 1, that there is an interruption in the incision between a bi-planar incision 11 and two outer vertical partial incisions 16, which collectively form the corneal access incision 1.

The bi-planar incision 11 runs as a "tunnel" through the corneal tissue 6 from an outer boundary surface 61 of the corneal tissue 6 to an inner boundary surface 62 of the corneal tissue 6. The outer vertical partial incisions 16, running on both sides of the bi-planar incision from an outer boundary surface 61 toward the inner boundary surface 62, but not reaching said inner boundary surface, nor connected directly to the bi-planar incision 11, serve to improve the functioning of the access incision 1. They have a wedge-shaped design, which is obtained in each case by a continuous reduction in the laser beam intensity from the maximum value during a movement of the focal point of a femtosecond laser vertically into the corneal tissue 6 in order to generate such a vertical partial incision 16.

Figure 6:
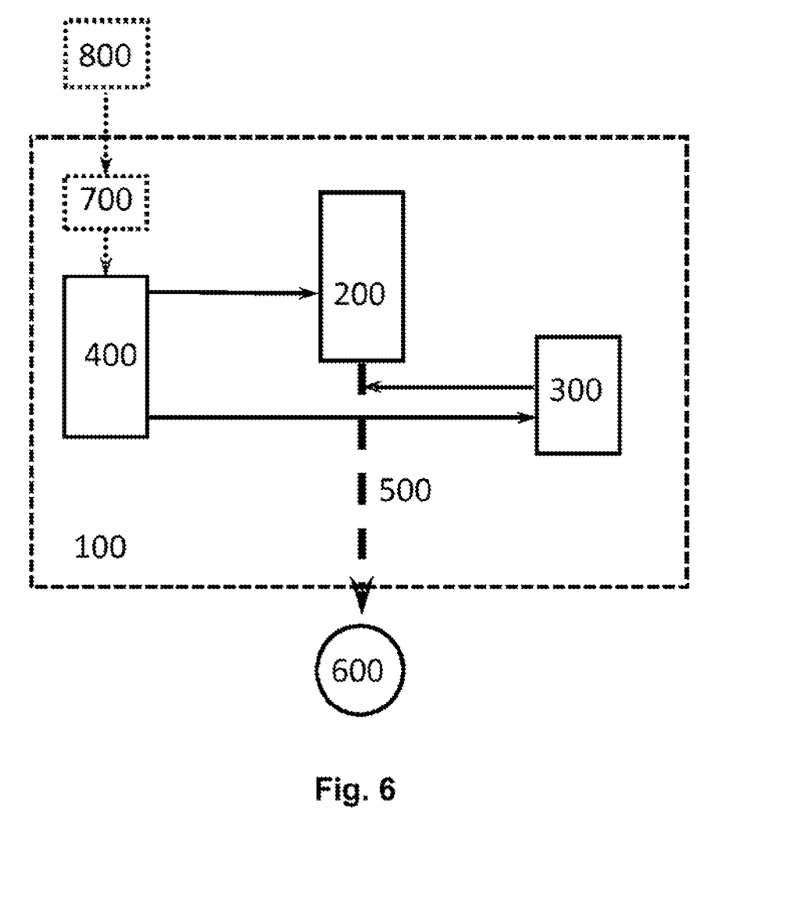
FIG. 6 depicts a fourth example embodiment of an ophthalmological therapy device according to the invention.

FIG. 6 illustrates a fourth example embodiment of an ophthalmological therapy device 100 according to the invention, having a laser system 200 for generating a femtosecond laser beam 500, a positioning system 300 for the spatial displacement of the focal point of the laser beam 500, and an integrated control system 400 for controlling the working parameters of the positioning system 300 and the laser system 200. This ophthalmological laser therapy device 100 includes an interface 700, with which the examination data, required by the program of the control system 400 for generating a fourth corneal access incision according to the invention, which were generated with an external examination system 800 in an examination of the eye 600 to be treated shortly before treatment with the ophthalmological therapy device 100, can be conveyed manually or automatically, depending on how the data are present—to the control system 400. In the manual input mode, the necessary values are called up successively via an input display screen, and entered by the operator.

Figure 7:
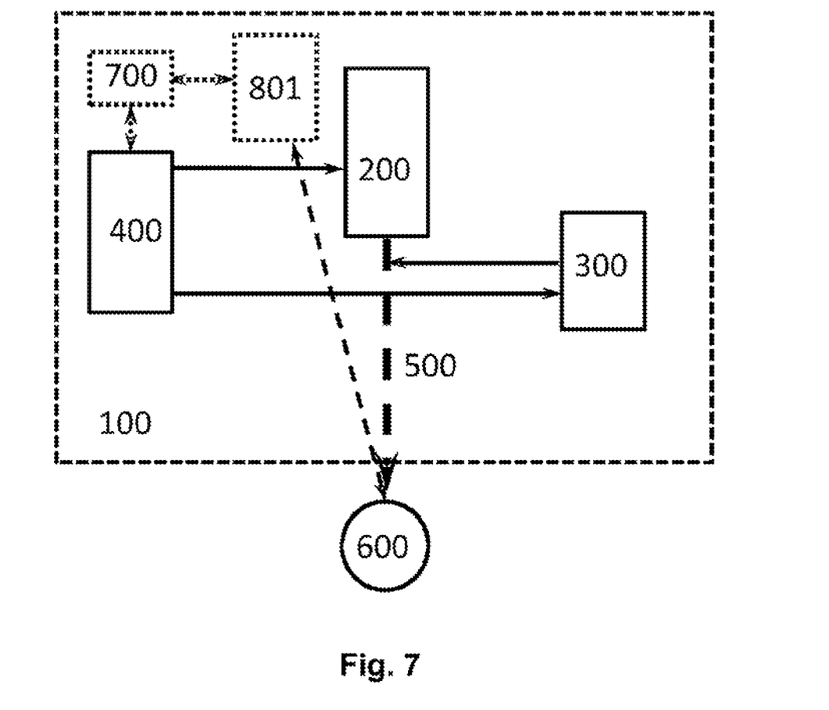
FIG. 7 depicts a fifth example embodiment of an ophthalmological therapy device according to the invention.

In contrast thereto, FIG. 7 shows a fifth example embodiment of an ophthalmological therapy device according to the invention. This fifth example embodiment differs from the fourth only in that it includes an integrated examination system 801, which generates the examination data that are conveyed via an interface 700 to the control system 400, and used there to create a fifth corneal access incision 1 according to the invention. The control system 400 can request, receive and process further examination data from the examination system 801 thereby during the step in which the corneal access incision 1 is generated, e.g. in the form of a confirmation of the success so far, or to correct or realign an incision that has already been initiated.

The features specified above and explained in various exemplary embodiments of the invention can be used not only in the combinations given by way of example, but also in other combinations or in and of themselves, without abandoning the scope of the present invention.

A description referring to a device feature applies analogously to the corresponding method regarding this feature, while method features represent functional features of the device descried herein accordingly.

The invention claimed is:

1. An ophthalmological laser therapy device, comprising:
a laser system that generates a pulsed laser beam;
a positioning system that spatially displaces a focal volume of the laser beam into a target region;
a control system that controls working parameters of the positioning system, working parameters of the laser system or both the working parameters of the positioning system and the working parameters of the laser system;
wherein the control system is programmed to generate a corneal access incision in corneal tissue of an eye through photodisruption, to modify the working parameters of the laser system, the working parameters of the positioning system or both the working parameters of the positioning system and the working parameters of the laser system as a function of a spatial position of the focal volume of the laser beam in the corneal tissue, such that the access incision varies in terms of width in the corneal tissue or the access incision both varies in terms of the width in the corneal tissue and is interrupted,
wherein the corneal access incision is formed as a passage or tunnel through the cornea from an outer boundary surface of the cornea to an inner boundary surface of the cornea without resection of tissue and through which a small diameter instrument may be inserted.

2. The ophthalmological laser therapy device according to claim 1, wherein the control system is further programmed to modify the working parameters such that a bi-planar incision and a vertical, wedge-shaped partial incision tapering toward an end, starting from the bi-planar incision, are generated in the corneal tissue.

3. The ophthalmological laser therapy device according to claim 1, wherein the control system is further programmed to modify the working parameters such that a bi-planar incision and, in the region of the bi-planar incision, an inner vertical partial incision, an outer vertical partial incision or both of the foregoing not directly connected to the bi-planar incision are generated in the corneal tissue.

4. The ophthalmological laser therapy device according to claim 1, wherein the laser system comprises a femtosecond (fs) laser system.

5. The ophthalmological laser therapy device according claim 1, wherein the control system comprises an interface that processes examination data of an eye from an examination system.

6. The ophthalmological laser therapy device according to claim 5, wherein the control system controls the generation of a corneal access incision by using examination data from the examination system.

7. The ophthalmological laser therapy device according to claim 1, further comprising an examination system that generates examination data of an eye.

8. The ophthalmological laser therapy device according to claim 7, wherein the control system controls the generation of a corneal access incision by using examination data from the examination system.

9. The ophthalmological laser therapy device according to claim 1, further comprising a positioning system, comprising at least one of the components: a stationary mirror, a rotatable mirror, a lens or a directional module.

* * * * *

UNITED STATES PATENT AND TRADEMARK OFFICE
CERTIFICATE OF CORRECTION

PATENT NO. : 10,653,557 B2
APPLICATION NO. : 15/553163
DATED : May 19, 2020
INVENTOR(S) : Michael Stefan Rill et al.

Page 1 of 1

It is certified that error appears in the above-identified patent and that said Letters Patent is hereby corrected as shown below:

In the Claims

Column 12, Line 20, delete "according" and insert --according to--

Signed and Sealed this
Third Day of November, 2020

Andrei Iancu
*Director of the United States Patent and Trademark Office*